(12) United States Patent
Lucas, Jr. et al.

(10) Patent No.: US 7,819,118 B2
(45) Date of Patent: Oct. 26, 2010

(54) MEDICAL GAS DELIVERY METHOD AND APPARATUS

(75) Inventors: James L. Lucas, Jr., Elyria, OH (US);
Donald M. Simo, Vermilion, OH (US);
Paul R. Eagan, Milton, FL (US)

(73) Assignee: Tri-Tech Medical Inc., Avon, OH (US)

( * ) Notice: Subject to any disclaimer, the term of this patent is extended or adjusted under 35 U.S.C. 154(b) by 768 days.

(21) Appl. No.: 11/775,954

(22) Filed: Jul. 11, 2007

(65) Prior Publication Data
US 2008/0011299 A1    Jan. 17, 2008

Related U.S. Application Data

(60) Provisional application No. 60/807,394, filed on Jul. 14, 2006.

(51) Int. Cl.
*A61M 11/00* (2006.01)
(52) U.S. Cl. .................. 128/204.18; 137/14; 137/360; 137/382; 137/606
(58) Field of Classification Search ............ 128/204.18; 137/14, 360, 382, 606, 597, 1; 251/89
See application file for complete search history.

(56) References Cited

U.S. PATENT DOCUMENTS

| 4,546,794 | A | * | 10/1985 | Ball | 137/599.03 |
|---|---|---|---|---|---|
| 4,989,637 | A | * | 2/1991 | Dittrich | 137/599.03 |
| 4,991,820 | A | * | 2/1991 | Kohn et al. | 251/149.5 |
| 5,435,342 | A | * | 7/1995 | Kohn et al. | 137/360 |
| 5,522,420 | A | * | 6/1996 | Martin | 137/343 |
| 5,950,675 | A | * | 9/1999 | Minami et al. | 137/606 |
| 6,305,400 | B1 | | 10/2001 | Simo et al. | |
| 6,484,747 | B2 | * | 11/2002 | Bridgers | 137/355.17 |
| 7,159,608 | B1 | * | 1/2007 | Lucas et al. | 137/341 |

* cited by examiner

*Primary Examiner*—Steven O Douglas
(74) *Attorney, Agent, or Firm*—Christopher L. Parmelee; Walker & Jocke

(57) ABSTRACT

A method is provided for connecting a secondary source of a medical gas to a control panel of a medical gas supply. The control panel is connected in the system fluidly between primary supply sources holding types of medical gas and gas outlets for the delivery of the respective types of medical gas to devices in a medical facility. For each gas type, the control panel houses a respective shut off valve. The shut-off valve may be closed to isolate the upstream source from the downstream components. A fitting is installed in place of an existing pressure gauge in the control panel. The fitting provides ports for at least one gas specific DISS coupler and further components such as a pressure gauge and transducers. The fitting has a configuration such that when installed, the fitting does not interfere with closing the cover to the control panel.

11 Claims, 16 Drawing Sheets

MEDICAL GAS DELIVERY METHOD AND APPARATUS

CROSS REFERENCE TO RELATED APPLICATIONS

This application claims benefit of U.S. Provisional Application Ser. No. 60/807,394 filed Jul. 14, 2006, which is hereby incorporated herein by reference.

TECHNICAL FIELD

Embodiments of inventions described herein relate to the supply of medical gases in the environment of a medical facility. More specifically, one or more embodiments are concerned with connecting a secondary gas supply to a medical gas supply system in a safe and efficient manner in the event that the primary supply is unable or unsuitable to deliver gas as required. Furthermore one or more embodiments: provide a source and method to access medical gases in the event of an emergency; expand an existing system to support additional patient needs in the event of a catastrophic event; and provide a safer more efficient means for testing medical gas alarms monitoring the medical gas piping system.

BACKGROUND ART

It is often necessary for trained personnel to provide a variety of gases of medical quality in a medical facility. Examples of such gases include medical air, oxygen, nitrogen, nitrous oxide, and carbon dioxide. Systems are also often installed in medical facilities which provide vacuum or gas evacuation. Gas service may be provided through a system which delivers the gas throughout a facility or portions or zones thereof. A number of primary supply sources of gas are used to deliver gas through outlet ports positioned at locations within the medical facility. The delivery system for each type of gas commonly includes manifolds with appropriate shut-off valves and pressure gauges. The delivery system also commonly includes at least one pressure regulator, check valve, and piping supply lines connecting the elements of the system. The primary supply source for each gas may be located in a secure area in the interior of the medical facility. Alternatively a primary supply source may be located at the exterior of the facility for maintenance by outside vendors providing the various gases.

It is critically important that the correct gas at the proper pressure be supplied when required from a medical gas supply system. Great effort is taken to assure that the various gases supplied are clearly marked at all locations. The possibility for delivery of the wrong gas at an incorrect location must be minimized. The pressure of each gas delivered may also be appropriately monitored throughout the system.

There are occasions which may require a secondary gas source to be connected to the gas delivery system of a medical facility. These instances might involve an emergency, a need for maintenance, a requirement of inspection, certification testing or service. One method of connecting the secondary gas source involves connecting the secondary gas source to the system through a hose to a conduit in the facility which normally serves as an outlet. Such an arrangement, known as backfeeding in the industry, is undesirable according to the National Fire Protection Association (NFPA), the regulatory agency responsible for medical gas piping standards. Such a connection, according to NFPA, should not be done.

Gases delivered by medical gas systems are generally at relatively low pressures. Typical desired pressure levels are 50 psi for oxygen, nitrous oxide, carbon dioxide and medical air, 180 psi for nitrogen, and 15 in/Hg to 25 in/Hg for vacuum or gas evacuation. Bottled gases by comparison have considerably higher pressures, commonly about 2000 psi. If the wrong gas were delivered to the wrong supply line through backfeeding, incorrect pressure or flows in portions of the system may occur. Such incorrect pressures and flows may place equipment and personnel at risk.

The medical system for each gas type is designed to provide gas flow from the primary source toward the various outlets and devices which utilize the gas within the medical facility. Gas should not be allowed to flow in a direction opposite to that for which the equipment was designed. Reverse operation requires a user to thoroughly understand every component of the system and what is necessary to safely accomplish reverse flow. It is often difficult to conduct such an analysis when many types of devices may be connected to the system.

For these reasons NFPA has disapproved of the practice of backfeeding of gas supply lines. Despite the NFPA position, personnel in medical facilities when faced with the necessity of keeping gas systems in operation are forced to use such backfeeding connections. In 1996 NFPA took the position that emergency service of an oxygen supply could be provided by a low pressure inlet located in the main supply line. This inlet is required to be located at the exterior of the medical facility. The use of such an inlet is authorized only for use to achieve an emergency supply of oxygen and is not to be used in the case of inspection/certification. Since this emergency inlet port is not required to be retrofit into existing "grandfathered" systems, most medical facilities are not equipped with this capability. Such an arrangement is of no help when the problem in the system is something other than the main supply, such as a system break inside the medical facility. In addition, gas delivery systems are normally divided into zones. This port does not allow gas service to be selectively supported or inspection/certification activities to be performed by selected zones. As a result, even in oxygen systems which have such a port the practice of backfeeding is sometimes necessary.

Thus there exists a need for an apparatus and method for connecting a secondary supply of a medical gas to a medical gas supply system. There further exists a need for an apparatus and method of connecting such a secondary supply of medical gas in a quick and reliable manner, which can be connected to selected zones of the supply system and which does not require backfeeding of any portion of the gas supply system.

DISCLOSURE OF INVENTION

An exemplary embodiment may include a method of connecting a secondary gas source to a medical gas supply system in a medical facility. Gas piping carries each gas from a primary supply source, through supply lines and to various outlets and devices in the medical facility or portions thereof. A valve box referred to herein as a control panel is positioned in a main supply line. The main supply line may supply the entire system or a portion or zone within the system. The control panel houses a shut off valve which when closed separates the primary supply source from the balance of the system. Also housed within the control panel is an inlet port for connection to a secondary gas supply. The inlet port is fluidly connected to the system downstream and/or upstream of the valve. Access to the valve and the inlet port in the control panel is normally prevented by a removable face on the control panel. The control panel is constructed so that if the removable face is in position on the control panel it is required that the valve is in an open condition so that the system is being supplied from the primary gas supply source.

In situations when it is necessary to supply the system or a respective zone controlled from the control panel from a secondary gas supply source, the face of the control panel is removed. The valve in the interior of the control panel is closed. This isolates the primary supply source and other system components upstream of the control panel from the system and devices downstream of the control panel. The secondary gas supply source is connected to the inlet housed in the control panel. Gas from the secondary source is allowed into the system in a controlled fashion through the inlet to maintain the gas supply to downstream components. This inlet port must be provided with a gas specific connection such as a threaded coupler using a diameter indexed safety system (DISS) or any style of quick connect fittings common to the industry. Only a mating gas specific connection can be connected to the port. Mounting of the mating specific threaded coupler to the port is operative to open a demand check valve to place the secondary gas supply in fluid communication with the system. This arrangement increases the probability that only a secondary gas source suitable to use in the system can be connected to a specific inlet port.

An exemplary embodiment includes a method of upgrading an existing control panel of a medical gas delivery system to include a gas specific DISS threaded coupler. Such existing control panels typically comprise an enclosure and a cover (e.g. door, window, removable panel) operative to close an opening to the enclosure. The enclosure includes therein a least one valve and first and second pipelines in operative connection with each respective end of the at least one valve. The first and second pipelines each include a front facing side which faces the opening to the enclosure. The front facing side of the first pipeline may include a threaded opening therein. A pressure gauge is typically mounted in the threaded opening and is typically viewable through a transparent portion of the cover to the enclose.

In this described embodiment, the method of upgrading the control panel may include removing the pressure gauge from the threaded opening of the first pipeline. This described method then includes mounting a fitting to the threaded opening of the first pipeline. The fitting includes a body and a threaded projection extending from the body. The threaded projection is installed into the threaded opening of the first pipeline. The body also includes at least two ports therein which are in fluid communication with an opening through the threaded projection. A first one of the ports includes a gas specific DISS threaded coupler mounted thereto, which extends from the fitting in a direction that is substantially perpendicular to a longitudinal axis of the projection of the fitting. A second one of the ports may include a second pressure gauge which extends from the fitting in a direction that is substantially perpendicular to the longitudinal axis of the projection of the fitting. After being mounted to the threaded opening of the first pipeline, the fitting is of a size and configuration which ensures that the gas specific DISS threaded coupler, and the second pressure gauge do not extend through the opening of the enclosure.

In this described embodiment, the method may include connecting a secondary gas source to the gas specific DISS threaded coupler. The secondary gas source may include a pressure vessel with a valve, a regulator, and a mating specific threaded coupler adapted to mount to the gas specific DISS threaded coupler and place the secondary gas source in fluid communication with the first pipeline. The method may further includes opening the valve on the pressure vessel so as to deliver gas from the pressure vessel into the first pipeline. The method may also include closing the valve of the medical gas delivery system and controlling the pressure of gas applied from the pressure vessel into the medical gas system through use of the regulator associated with the pressure vessel. Examples of control panels that have been adapted to include gas specific DISS couplers is found in the inventor's U.S. Pat. No. 6,305,400 B1 which is hereby incorporated herein by reference.

In an alternative embodiment, once the fitting has been mounted to an existing control panel, as described previously, the gas specific DISS threaded coupler my be used to mount an additional medical gas outlet port to the control panel. For example, a further exemplary embodiment may include connecting a secondary gas outlet to the gas specific DISS threaded coupler. The secondary gas outlet may include at least one outlet port and a mating specific threaded coupler adapted to mount to the gas specific DISS threaded coupler and place the secondary gas outlet in fluid communication with the first pipeline. The method may further include connecting a gas delivery mask to the at least one outlet port and providing a medical gas to a patient through the gas delivery mask. In this described alternative exemplary embodiment, the secondary gas outlet may include a plurality of outlet ports, wherein each outlet port is mounted to a wall of a hallway to form a medical gas rail. In an emergency in which large numbers of patients require medical gases, the method may include connecting a plurality of the gas delivery masks to the plurality of outlet ports. Patients located in hallways of the hospital or in waiting rooms may then be provided with medical gas through the delivery masks connected to the medical gas rail.

In addition, the described system is capable of being quickly adapted in an emergency or non-emergency setting to provide medical gases for all medical and clinical needs. For example, the described system could be quickly adapted to provide medical gases in the operating room area for emergency surgeries.

It should also be understood that exemplary embodiments may further include using the above described fitting in new equipment such as new control panels for medial gas delivery systems. As discussed previously the fitting may comprise a body including an internal cavity through which medical gases are capable of flowing. The body of the fitting may also include a threaded projection extending from the body. This threaded projection includes an opening therein to the cavity in the body. In addition, this threaded projection may be adapted to connect to one of one or more threaded openings of in a medical gas pipeline in the control panel.

The body of the fitting may also include at least two ports. Each of the ports includes an opening therein to the cavity in the body. A first one of the ports is adapted to receive a gas specific DISS threaded coupler mounted thereto, which extends from the fitting in a direction that is substantially perpendicular to a longitudinal axis of the projection of the fitting. A second one of the ports is adapted to receive a pressure gauge mounted thereto which extends from the fitting in a direction that is substantially perpendicular to the longitudinal axis of the projection of the fitting. In this described exemplary embodiment, the fitting has a size, such that when the fitting is mounted to the threaded opening of the medical gas pipeline, the fitting places the gas specific DISS threaded coupler and the pressure gauge in positions which do not extend the DISS threaded coupler and the pressure gauge through an opening of an enclosure of the control panel.

In exemplary embodiments of a control panel that includes the above described fitting, the control panel may be produced with the gas specific DISS threaded coupler in operative connection with the first one of the ports of the fitting. Also the control panel may be produced with the pressure gauge in operative connection with the second one of the ports of the fitting. As discussed previously, such a control panel may be comprised of the enclosure and the cover operative to close the opening to the enclosure. Such a control panel also includes a least one valve and first and second pipelines in operative connection with each respective end of the at least one valve. The first and second pipelines each include a front facing side which faces the opening to the enclosure. The front facing side of one or both of the pipelines may include a threaded opening therein. The threaded projections of one or more of the described fittings may be in operative connection with the threaded opening(s) in one or both of the pipelines for one or more valves of the control panel. As discussed previously, when the control panel is configured in this manner, the DISS threaded coupler(s) and the pressure gauge(s) mounted to each fitting in the control panel will not extend through the opening of the enclosure of the control panel. Also in exemplary embodiments, additional DISS threaded couplers may be mounted to the described fittings in the control panel. Also one or more transducers may be mounted in the control panel which are connected via a hose or other conduit to the DISS threaded coupler(s) of the described fitting(s).

BEST MODES FOR CARRYING OUT INVENTION

Figure 1:
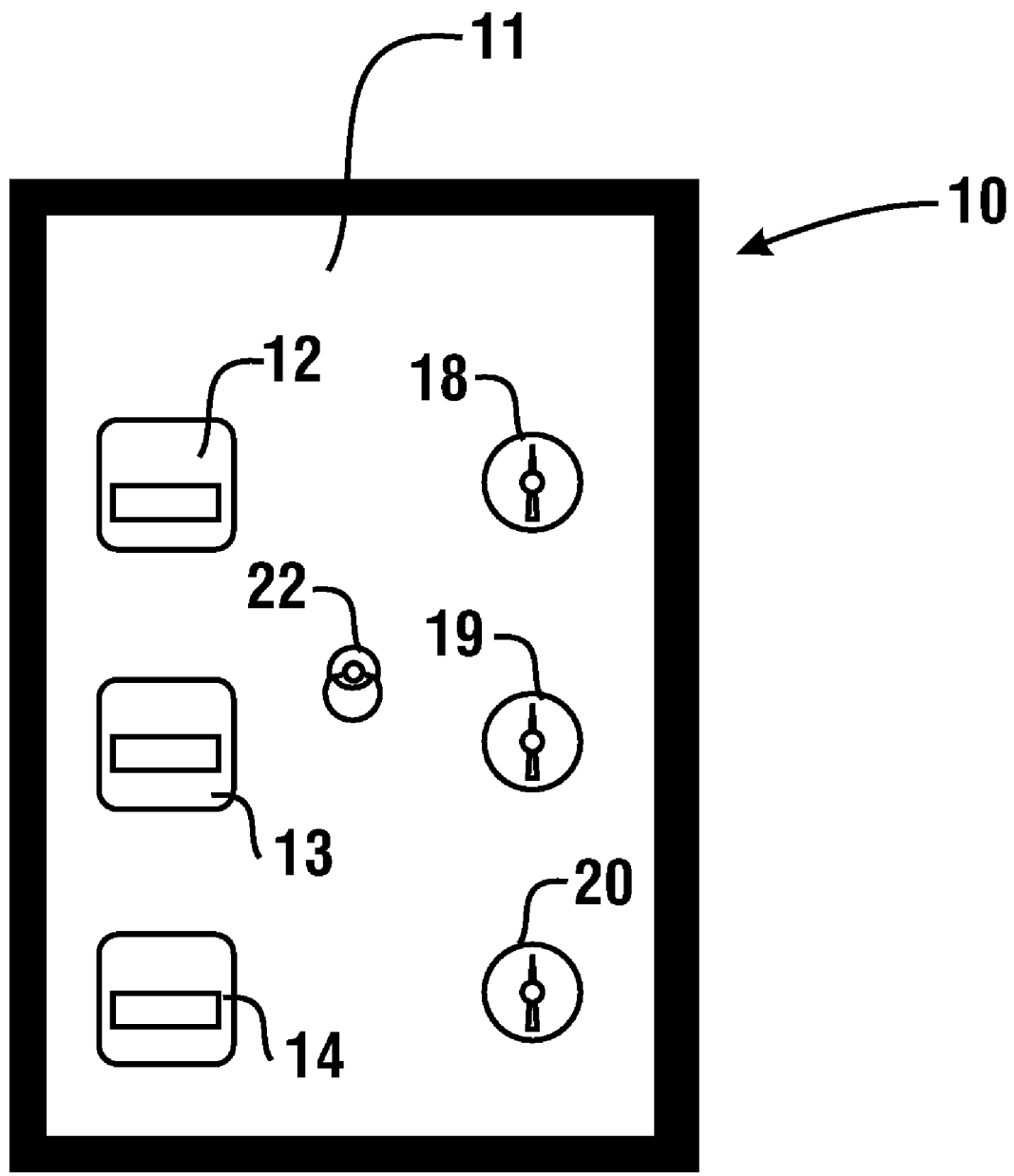
FIG. 1 is a plan view of a control panel for zone shut-off valves in a medical gas supply system.

Referring now to the drawings and particularly to FIG. 1 there is shown therein a valve box 10 which is referred to herein as a control panel 10. Control panel 10 is designed to be installed in a medical gas supply system in a medical facility which employs an exemplary embodiment. The panel 10 includes a face 11. Panel 10 shown in this example is designed to accommodate controls and fluid connections for three separate gases. Each control panel installation in a gas supply system may need to accommodate more or less than three gases. The control panel may be specifically designed for the number of gases required to flow therethrough. In the exemplary embodiment face 11 has gas identification placards 12, 13 and 14 for each gas which passes therethrough. The gas identification placards 12, 13 and 14 may include specific markings and indicia which indicate the particular medical gas which flows in each line and the area of the facility served by each valve.

In the exemplary embodiment of control panel 10 faces of pressure gauges 18, 19 and 20, one for each gas, are visible through the face 11. Pressure gauges 18, 19 and 20 monitor pressure at the control panel location in the system. Gas types commonly provided through the use of panel 10 in a medical facility include (but are not limited to) medical air, oxygen, nitrogen, nitrous oxide, carbon dioxide and vacuum or gas evacuation. In the case of oxygen, nitrous oxide, carbon dioxide and medical air, the pressure gauge face commonly reads in a range from 0 to 100 psi. For nitrogen the gauge face commonly reads in a range from 0 to 300 psi. For vacuum or gas evacuation the gauge face reads in a range from 0 to 30 in/Hg. It should be understood that while in the exemplary embodiment gauges are used as pressure indicators, in other embodiments other types of pressure indicating devices may be used. The frame of the face 11 of the panel is attached by screws which releasably secures the frame of the face to the control panel 10. In the exemplary embodiment the face may be removed from the panel by pulling on a ring 22. The face of the control panel is reinstalled by moving the panel into position. In embodiments various releasable latching mechanisms may be used to secure the face to the control panel.

Figure 2:
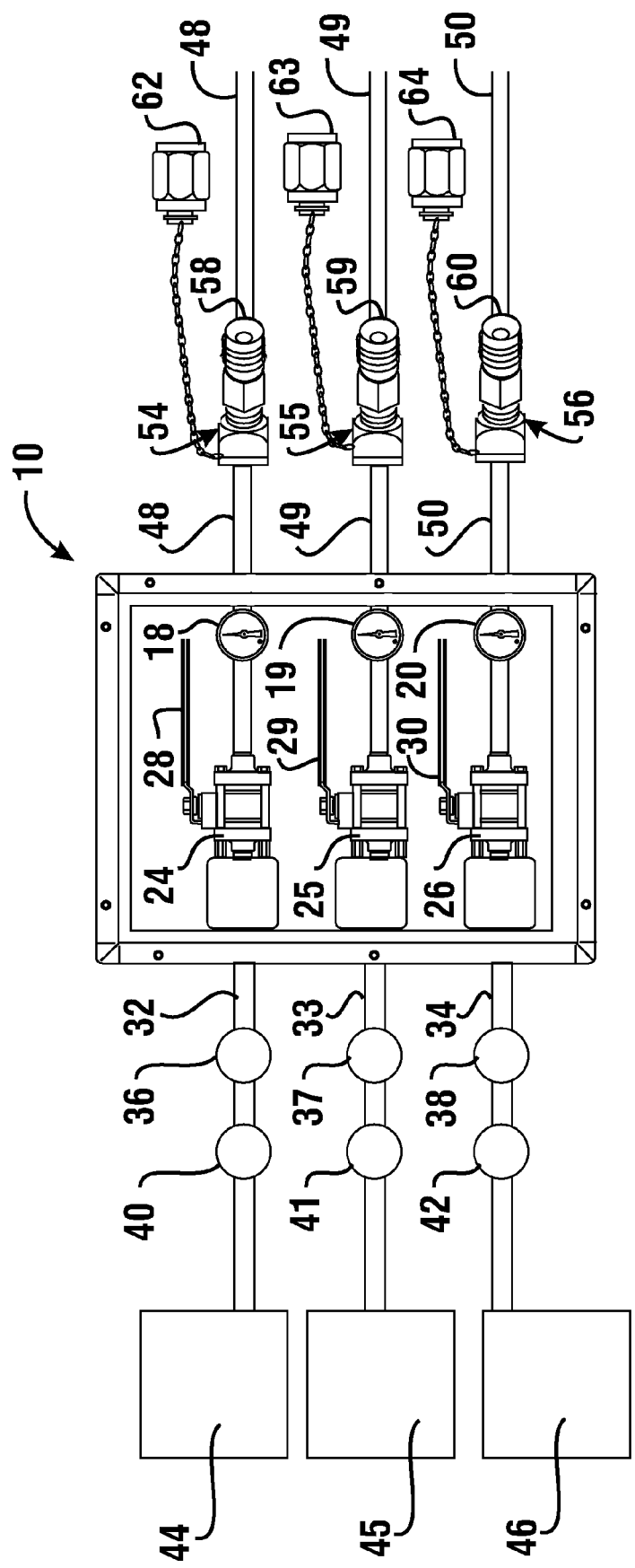
FIG. 2 is an exemplary schematic diagram representative of a medical gas supply system.

FIG. 2 illustrates the control panel 10 installed in a simplified exemplary embodiment of a medical gas delivery system. Face 11 of the panel has been removed to reveal the contents thereof. Pressure gauges 18, 19 and 20 are located within the enclosure of panel 10. Additionally, shut-off valves 24, 25 and 26, one for each of the gas lines, are housed within the panel. The pressure gauges are positioned in the panel on the downstream side of the valves.

The shut-off valves 24, 25 and 26 in the exemplary embodiment may be three-piece in-line repairable ball type valves. In the exemplary embodiment they are constructed of bronze and have Teflon® seats and seals. The valves are commonly rated at 600 psi. Each valve includes adjustable packing and a blowout proof stem. Valves 24, 25 and 26 are operated by lever handles 28, 29 and 30. Operation of the valve from fully open to fully closed requires only one quarter of a full turn of the handle. The control panel may be constructed so that the handle extends outward when in the closed position. As a result the face must be removed from the panel when a valve is in a closed position. This is useful in enabling quick visual inspection of the conditions of the valves.

A control panel 10 may be used as part of a gas feed system zone manifold in a plurality of zones required throughout the medical facility. The facility is sectioned into zones requiring similar gases or uses with a valve controlling the supply of gas to each zone. Control panels may also be positioned for specific sub-zones or areas within the facility. The zone arrangement simplifies inspection and maintenance in that only a specific zone could be incapacitated or require gas delivery from a secondary source. By pulling the ring 22 and removing face 11 of the control panel, one or more shut-off valves 24, 25 or 26 within the panel are enabled to be closed. By closing the appropriate valve a particular zone or line in the system could be isolated without interfering with the balance of the gas delivery system.

The exemplary control panel 10 includes primary source inlets 32, 33 and 34 upstream of the shut-off valves 24, 25 and 26. Pressure regulators 40, 41 and 42, one for each gas supply line, are connected upstream of the respective check-valve 36, 37 and 38. The pressure regulators are adjusted to supply the particular gas within the desired pressure ranges as noted above.

A primary gas source 44, 45 and 46, is connected upstream of the respective pressure regulator 40, 41 and 42. One primary gas source is provided for each of the gases the system is to deliver. In an exemplary embodiment each primary gas source 44, 45 and 46 may include a pressure vessel accessible from the exterior of the facility. The primary gas sources are therefore readily available to agents of an outside vendor for the purpose of servicing and refilling. In alternative embodiments other primary sources such as compressors, oxygen concentrators or other devices which produce or deliver the medical gas may be used. In systems which supply vacuum, an appropriate vacuum pump or similar device is connected to a respective line.

The control panel 10 has outlets 48, 49 and 50 located downstream of the pressure gauges 18, 19 and 20. These outlets connect the control panel to the balance of the gas delivery system within the zone or other area controlled by the control panel. Outlet ports 54, 55 and 56 are shown connected to outlets 48, 49 and 50, respectively. These outlets are representative of a plurality of outlets that may be connected to the gas system in the zone controlled by panel 10. All of the individual elements of the gas delivery system are interconnected with appropriate piping. In the exemplary embodiment each outlet port 54, 55 and 56 includes a gas specific diameter indexed safety system (DISS) threaded coupler 58, 59 and 60. In such a system only a unique fitting size and/or coupling type is used in connection with each medical gas. These gas specific sizes and/or coupling types provide increased assurance that only the correctly mating gas apparatus is connected to the line.

In the exemplary system shown a mating threaded closure or cap 62, 63 and 64 is located closely adjacent to the respective coupler. The caps may be attached to an area adjacent each outlet port 54, 55 and 56 through the use of a chain or wire. This reduces the risk that a removed cap will be lost. Although shown unthreaded for purposes of clarity of description, caps 62, 63 and 64 must be engaged on threaded outlet ports 58, 59 and 60 whenever an apparatus is not engaged to the outlet. This arrangement minimizes the risk that foreign matter enters an outlet port 54, 55 and 56 to cause contamination of the system. However, it is to be understood that not all styles of outlets are threaded and therefore not all outlets require caps.

During normal conditions each required medical gas type is available at each primary gas source 44, 45 and 46 and the shut-off valves 24, 25 and 26 in the control panel are open. Medical personnel can access a particular gas line as needed. This is accomplished by attaching a desired apparatus to an outlet port 58, 59 or 60. Gas flows in the desired direction only from the source to the outlets at the proper pressure for the gas utilizing devices connected to the system.

In the event of a system failure in which any element of the system upstream of shut-off valve 24, 25 or 26 fails or requires service, face 11 of the control panel 10 is removed by pulling on the ring 22. The appropriate shut-off valve 24, 25 or 26 for the gas type involving the failure may then be closed. This would be the case if a primary gas source 44, 45 or 46 became empty or another system component upstream of the control panel malfunctioned. The appropriate shut-off valve 24, 25 or 26 is closed so the system is not contaminated and there is no flow backward toward the primary supply source. Closing the valve in the control panel also isolates the zone downstream of the control panel from the remainder of the system.

Figure 3:
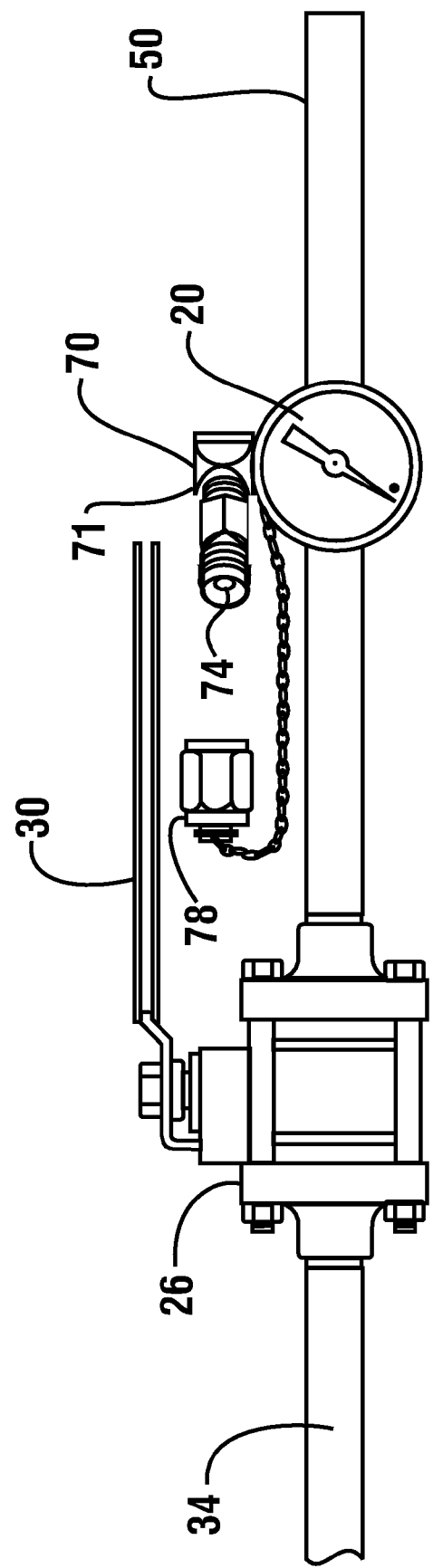
FIG. 3 is an exemplary schematic diagram representative of a manifold portion of the medical gas supply system including an inlet port.

In an exemplary embodiment, shown in FIG. 3, an inlet port 70 is connected in a gas conduit adjacent pressure gauge 20 within the control panel. The inlet port 70 may have a gas specific DISS threaded coupler 74 incorporating a demand check valve. A mating gas specific threaded closure or cap 78 serves to secure the inlet port when not in use to minimize the risk of contamination and provide additional protection from possible gas leakage. The cap 78 may be secured to inlet port 70 by a chain or wire when not in use. A demand check incorporated into the gas specific DISS threaded coupler 74 is connected to inlet port 70 for the purpose of assuring that pressurized gas may only flow in a direction into the inlet port 70 and serve as a primary seal when the system is in normal use. When shut-off valve 26 is closed, inlet port 74 may be used to supply the zone downstream of the control panel with gas from a secondary supply source.

Figure 4:
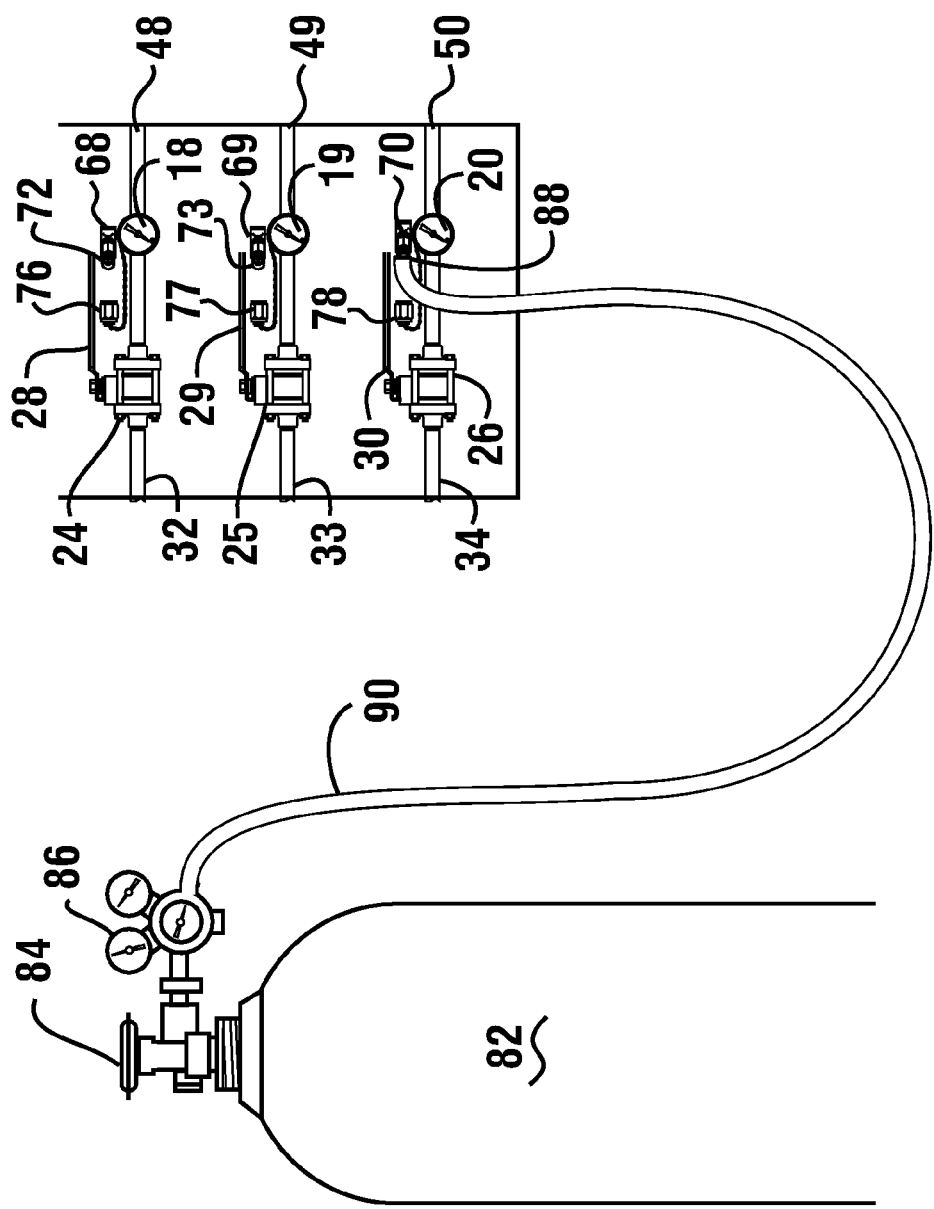
FIG. 4 is an exemplary schematic diagram representative of the manifold portion of the medical gas supply system including a secondary gas supply connected to the inlet port.

FIG. 4 shows a secondary source of gas, including a pressure vessel 82, connected to the inlet port 70 in the control panel 10. The secondary gas source includes a valve 84 and regulator 86 which control the pressure at which gas is delivered. The pressure vessel 82 is connected to deliver gas to inlet port 70 through a mating gas specific DISS threaded coupler 88. Coupler 88 in the embodiment shown is at the end of a hose 90 leading from regulator 86 of the secondary gas source. Once the proper connection of pressure vessel 82 to inlet port 70 has been made, valve 84 is opened to establish the fluid connection with the secondary source. Gauge 20 on the control panel provides an indication that the secondary source is supplying gas at the appropriate pressure. The secondary source supplies gas on an interim basis through the inlet port without backfeeding any portion of the system upstream of the valve 26 when in the closed position. As a result gas flows in the normal manner to all devices connected in the system downstream of the shut off valve. Valves 24 and 25 may be configured in a similar fashion.

In the exemplary embodiment inlet ports 68, 69 and 70 are connected to respective gas conduits in the control panel adjacent pressure gauges 18, 19 and 20. Each inlet port 68, 69 and 70 includes a gas specific DISS threaded coupler 72, 73 and 74 to minimize the risk of an incorrect connection. Mating caps 76, 77 and 78, respectively, correspond to the gas specific threaded coupler 72, 73 and 74 on the inlet ports to close the inlet ports when not in use. The control panel enables connecting a secondary source of gas for each gas type used in the system. Multiple gas sources and gas types may be connected through a single control panel.

The explanation herein has centered around maintaining gas supply despite a depleted or inoperative primary source of gas. In the event that maintenance, inspection or certification of a portion of the gas delivery system is required, a secondary gas source could be connected. Secondary gas sources may be used to supply selected zones which are isolated by the shut off valves from other zones. The demand check associated with the inlet for the secondary gas source assures that the primary and secondary sources may be connected and disconnected through the control panel in a manner that provides an uninterrupted supply of gas to the zone and which avoids loss of gas or damage to the system.

When gas flow from the primary source is to be restored, the shut-off valve connecting the gas source in the control panel may again be opened. The valve from the secondary source is then closed and the connection to the secondary inlet in the control panel disconnected. A demand valve in item 74, 58, 59 or 60 automatically closes preventing any escape of gas. The cap on the inlet is then installed. The face may then be attached to the control panel to indicate that all the valves within the panel are open.

The exemplary embodiment may also be used to facilitate the introduction of purging gases into a portion of the medical gas system. When additions or maintenance to medical gas systems are performed, NFPA 99 requires that purging gases such as nitrogen be placed into the medical gas pipeline prior to brazing. The purging gas reduces the formation of copper oxide during the brazing process by removing oxygen and moisture from the pipeline. In the exemplary embodiment the secondary input ports 68, 69, 70 provide readily available ports through which a purge gas may be input into the system.

Figure 5:
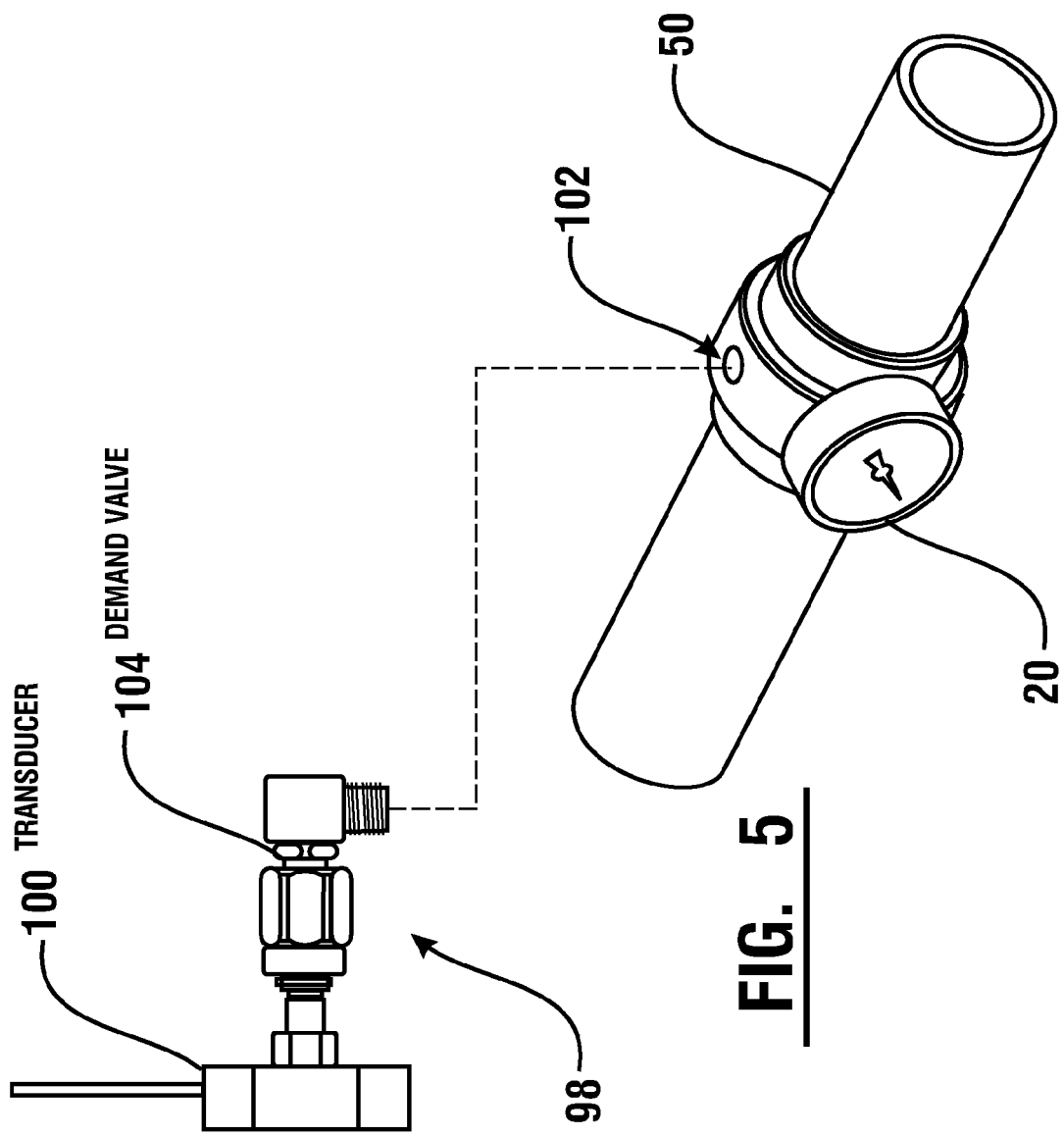
FIGS. 5 and 6 are exemplary schematic diagrams representative of connecting a transducer to the secondary gas inlet port of the medical gas supply system.

In addition to providing a gas specific secondary inlet for medical and purge gases, the exemplary embodiment of the control panel 10 may also be used for the remote connection of monitoring transducers. FIG. 5 shows a transducer assembly 98 being placed in connection with the inlet port 102. Here the transducer assembly includes at least one transducer 100 which is operative to remotely monitor properties of gases in the system. In the exemplary embodiment the transducer assembly further includes a demand check valve 104 which is operative to prevent outside gases and other contaminants from entering the system when the transducer is installed, repaired or replaced.

Figure 6:
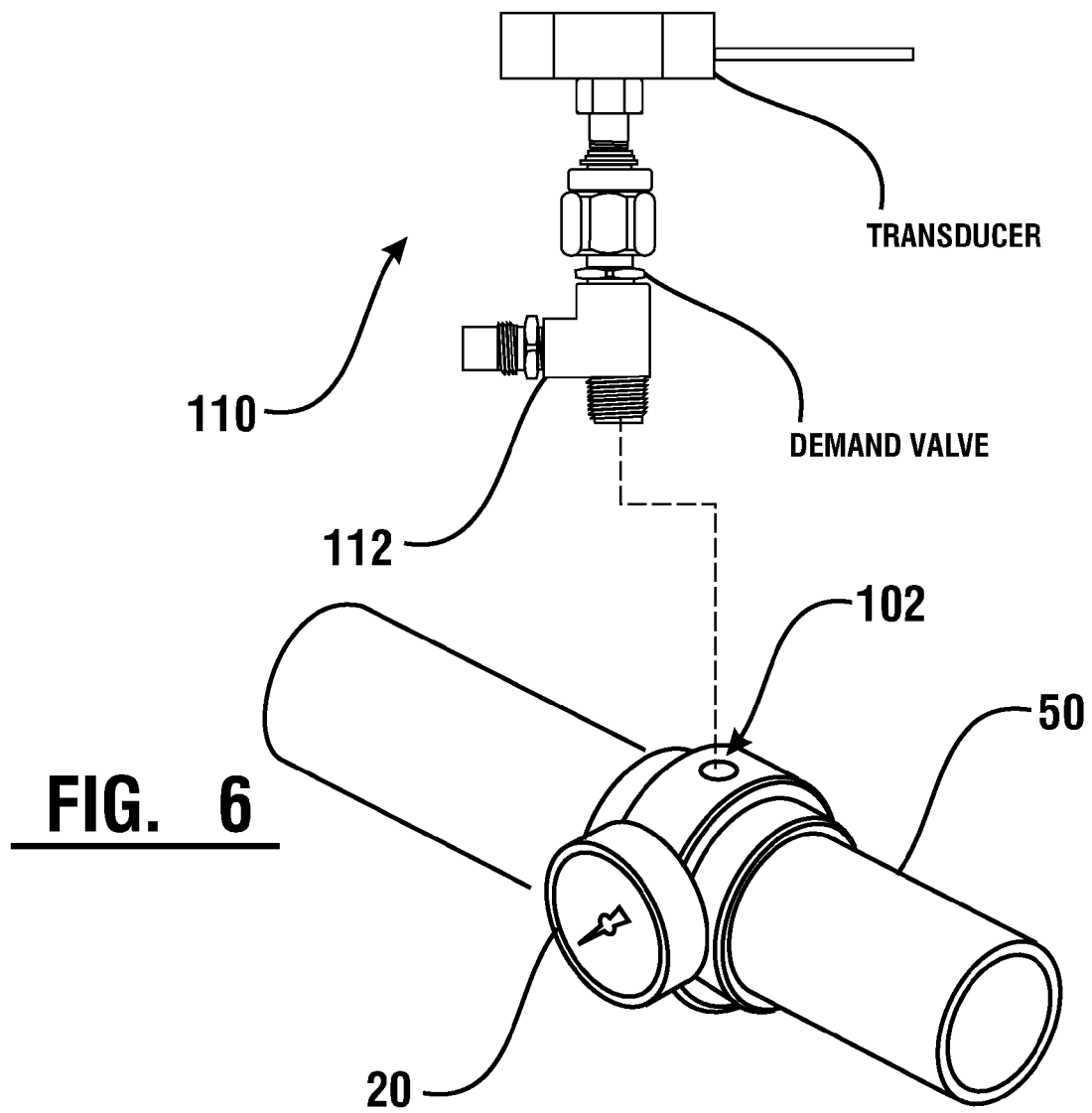

FIG. 6 is representative of an alternative transducer assembly 110, which includes a second connection end 112. The second connection end 112 enables the connection of addition transducers to the manifold. In addition the second connection end 112 can be configured to accept a secondary gas source by including a demand check valve and a DISS threaded coupler as previous described.

Figure 7:
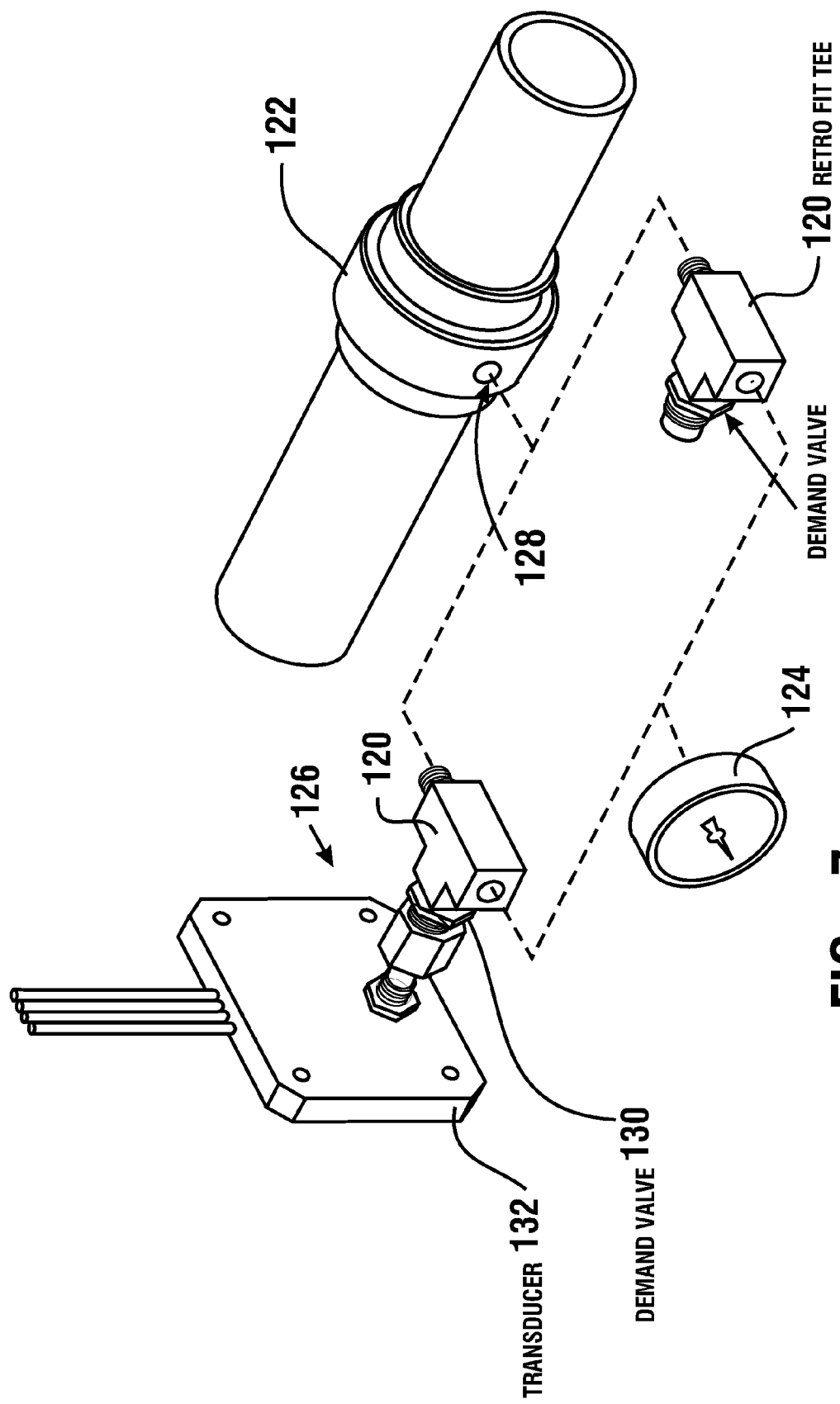
FIG. 7 is an exemplary schematic diagram representative of a transducer port retrofit assembly.

Embodiments may also encompass retrofitting existing medical gas supplies to include one or more transducers. As shown in FIG. 7 a retrofit transducer assembly 126 may be adapted for placement between a preexisting gauge 124 and a gas conduit 122. In this described embodiment the preexisting gauge 124 may be removed from a gauge port 128 of the conduit 122 and the transducer assembly 126 may be threaded in its place. The transducer assembly includes a tee connector 120 that is adapted to be threaded into the gauge port 128 and is adapted to accept the connection of the original gauge 124. As previously described the exemplary transducer assembly 126 further includes a demand check valve 130 and at least one transducer 132.

Configuring the exemplary control panel 10 to include remote transducers: enables transducers to be more easily found, replaced, and maintained; and facilitates the required annual testing of the medical gas alarm systems. Also the labeling of the exemplary embodiment of the control panel further facilities the identification of those areas, rooms, and/or zones which are being monitored by each transducer.

Figure 8:
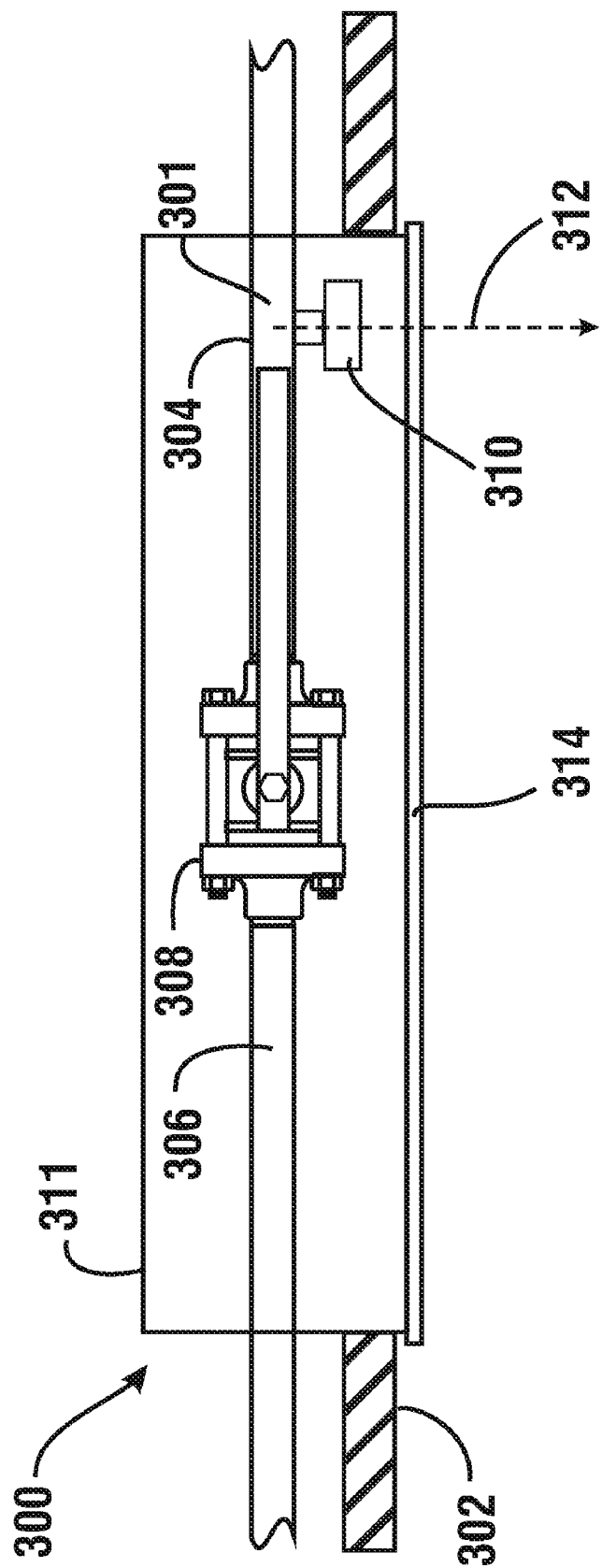
FIG. 8 shows a top plan cross-sectional view of an existing control panel mounted into a wall.

Control panels for zone shut-off valves in a medical gas supply system are often located in hallways of a hospital, and therefore are typically designed to have a relatively thin profile, so as to minimize the amount of distances the control panel extends from a hallway wall. As a result there is often very little room between a front cover (e.g. front door or window) of the control panel and components mounted inside the control panel such as valves and pressure gauges. FIG. 8 shows a top plan cross-sectional view of an existing control panel 300 mounted into a wall 302. This described control panel includes an enclosure 311 and a cover 314 operative to close an opening to the enclosure such as a door and/or window. Inside the enclosure the control panel includes two gas pipelines 304, 306 separated by at least one valve 308. At least one of the pipelines 304 includes a threaded opening 301 adapted to receive a pressure gauge 310. In this described embodiment, the threaded opening is positioned on a front facing side of the pipeline facing the cover 314 of the enclosure. The threaded opening is positioned on the front facing side of the pipeline to enable the pressure gauge 310 threaded therein to extend from the pipeline in a horizontal direction towards the cover 314 of the control panel.

Figure 9:
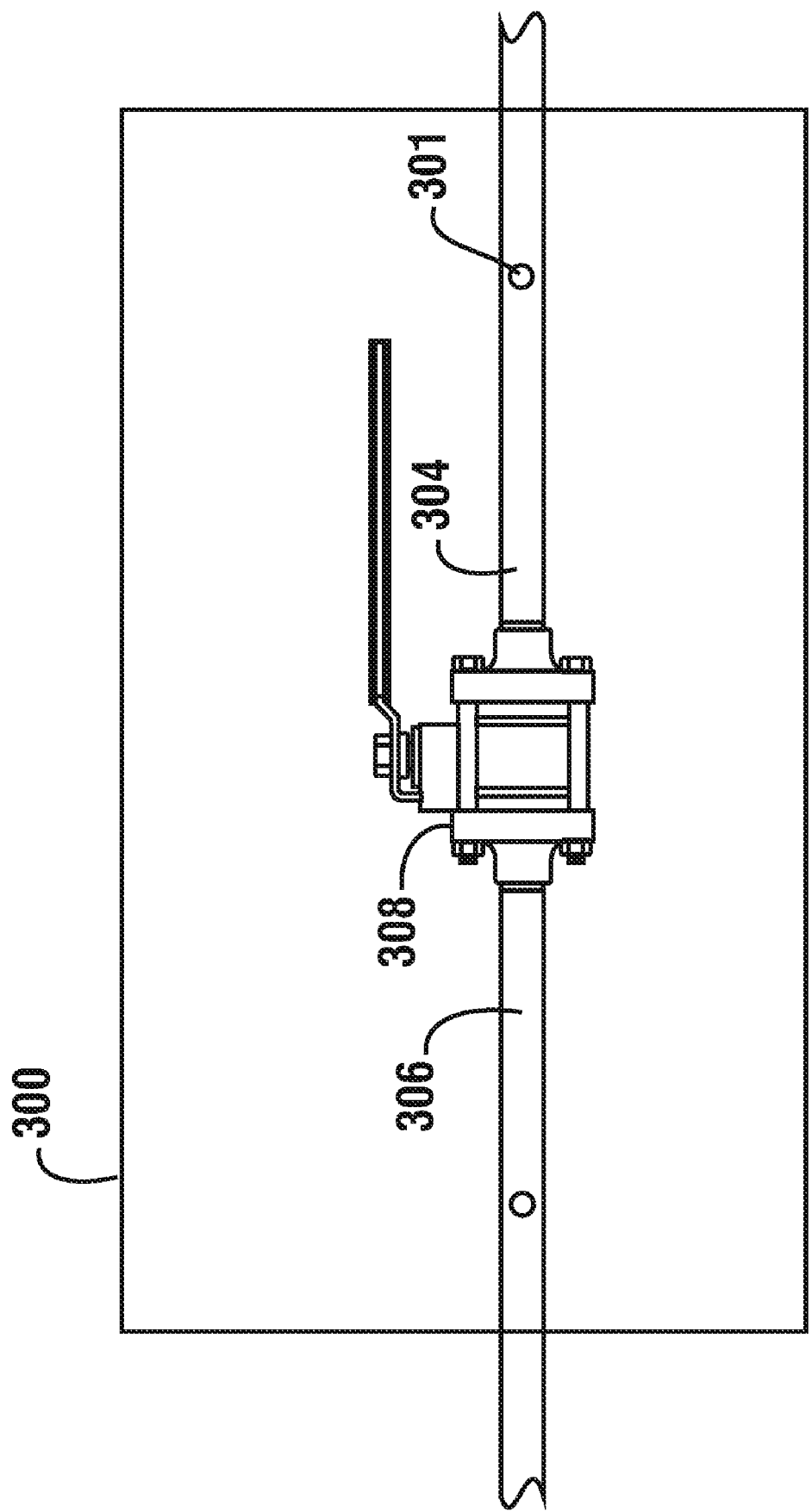
FIG. 9 shows a side plan view of the control panel mounted to the wall in which a pressure gauge has been removed.
Figure 10:
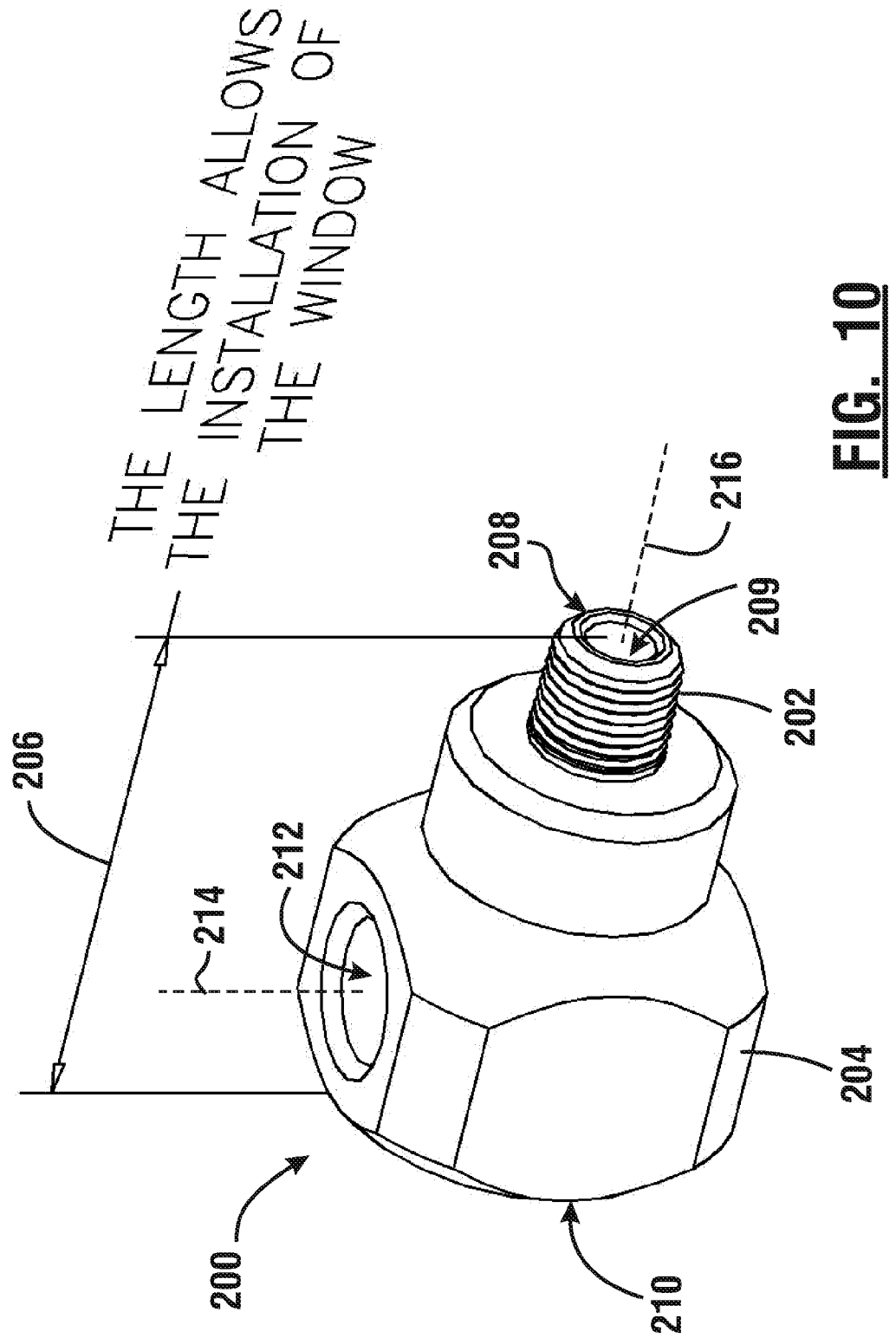
FIG. 10 shows an exemplary embodiment of a fitting adapted to mount in-place of the removed pressure gauge.

FIG. 9 shows a side plan view of the control panel 300 in which the pressure gauge has been removed from the threaded opening 301. To enable such an existing control panel 300 to be upgraded to include the above described gas specific DISS threaded couplers, an exemplary embodiment may include employing a new adapter fitting which is operative to mount in the existing threaded opening 301 previously used for a pressure gauge, but which fitting does not block the cover (e.g. door and/or window) of the control panel from being closed. FIG. 10 shows an example of such a fitting 200. The fitting includes a body 204 with an internal cavity therein through which medical gases are capable of flowing. The fitting further includes a threaded projection 202 extending from the body, which projection is adapted to be threaded into the existing threaded opening 301 in an existing control panel 300. The threaded projection includes an opening 209 to the internal cavity of the body.

In this described embodiment, the fitting is adapted to have a length 206 between the end of the projection 208 and the opposed end 210 of the body which enables all of the fitting to be located within the control panel such that the cover of the control panel may be closed when the fitting is mounted to a threaded opening 301 in the control panel.

Figure 11:
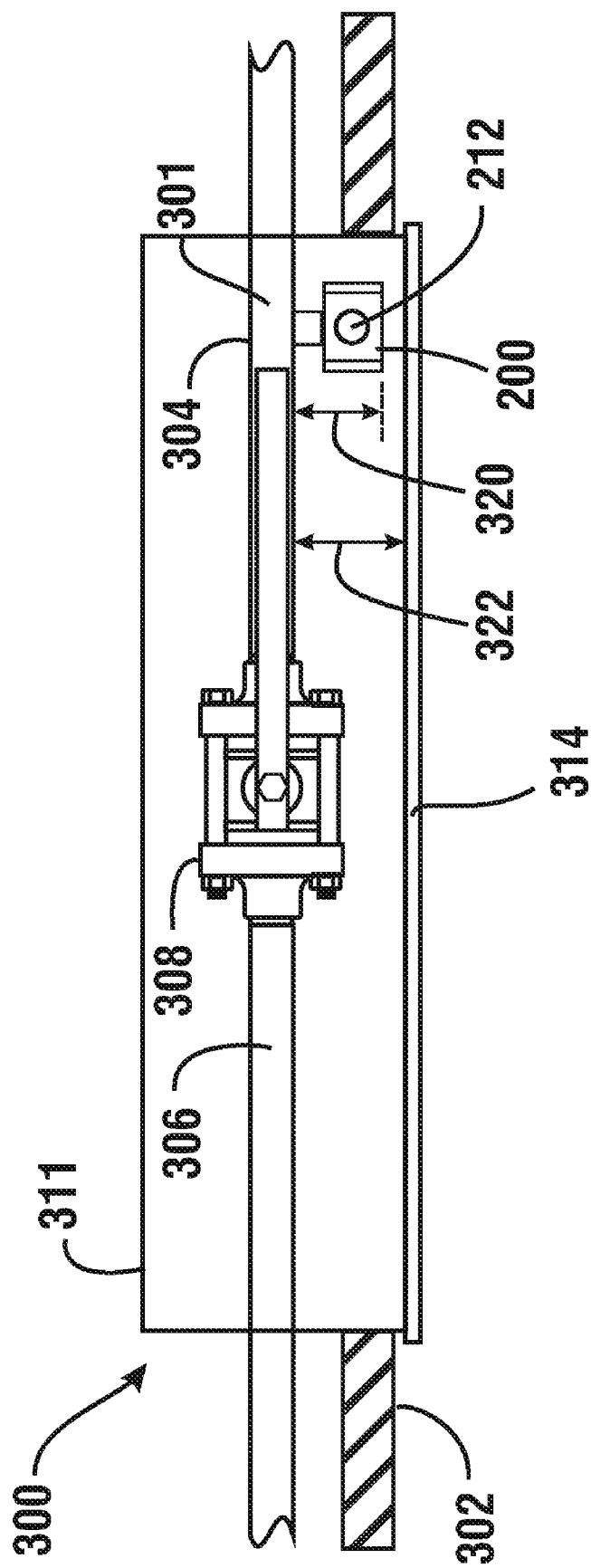
FIG. 11 shows a top plan cross-sectional view of the control panel with the new fitting threaded into a threaded opening previously used for mounting the removed pressure gauge.

FIG. 11 shows a top plan cross-sectional view of the control panel with the new fitting 200 threaded into the threaded opening 301 (FIG. 9) previously used for a pressure gauge. When mounted in this manner, the fitting extends from the pipeline 304 a distance 320 which is less than the distance 322 between the pipeline 304 and an inside surface of the cover 314 of the control panel.

Referring back to FIG. 10, the body 204 of the fitting 200 includes at least one port 212 which extends into the body to the internal cavity of the body. The at least one port 212 is orientated such that a longitudinal axis 214 of the port extends in a direction that is substantially perpendicular to the longitudinal axis 216 (FIG. 12) of the projection 202 and/or extends in a direction that is substantially parallel to the inner surface of the cover of the control panel when mounted to the threaded opening 301 in the side of the pipeline in the control panel.

Figure 12:
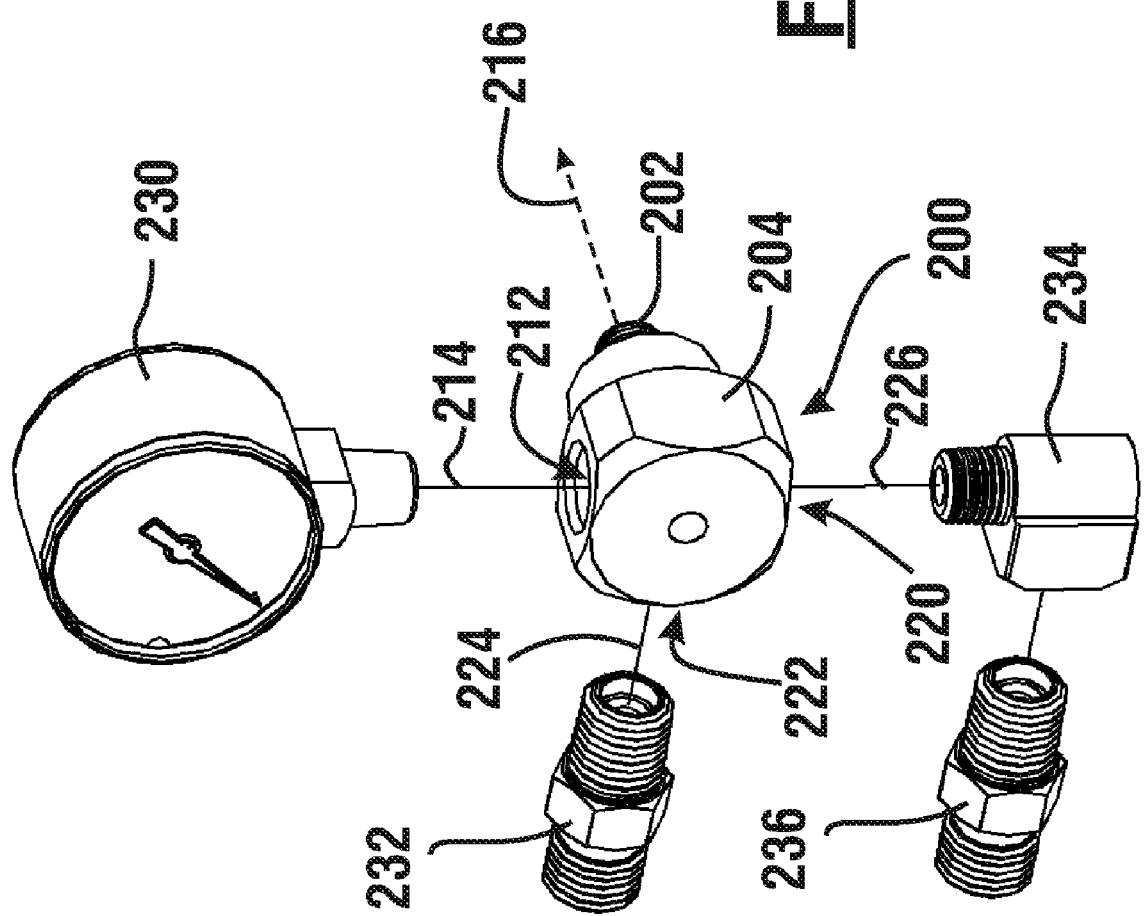
FIG. 12 shows a schematic view of the described fitting and components which may be mounted thereto.

FIG. 12 shows a schematic view of the described fitting 200 and components which may be mounted thereto. In this described embodiment, the body of the fitting 200 includes three ports 212, 220, 222 which are adapted to mount components so as to orientate respective longitudinal axes 214, 226, 224 of the components in directions which extend substantially radial with respect to the longitudinal axis 216 of the threaded protection 202 and/or which extend substantially parallel to the inner surface of the cover of the control panel when mounted to the threaded opening 301 (FIG. 9) in the control panel.

As shown in FIG. 12, various components may be mounted to the ports 212, 220, 222 of the fitting 200. Such components may include a pressure gauge 230, a gas specific DISS threaded coupler 232, transducers and other medical gas related fittings and/or components. In addition an elbow coupler 234 or other coupler may be mounted to a port of the fitting 200 to enable other components to extend from the fitting in directions that are not radial with respect to the longitudinal axis 216 of threaded projection 202. For example as shown in FIG. 12, a second gas specific DISS threaded coupler 236 may be mounted to the elbow coupler 234 so that it extends parallel to the first gas specific DISS threaded coupler 232 and parallel to the inner surface of the cover of the control panel when mounted to the threaded opening 301 (FIG. 9) in the control panel.

Figure 13:
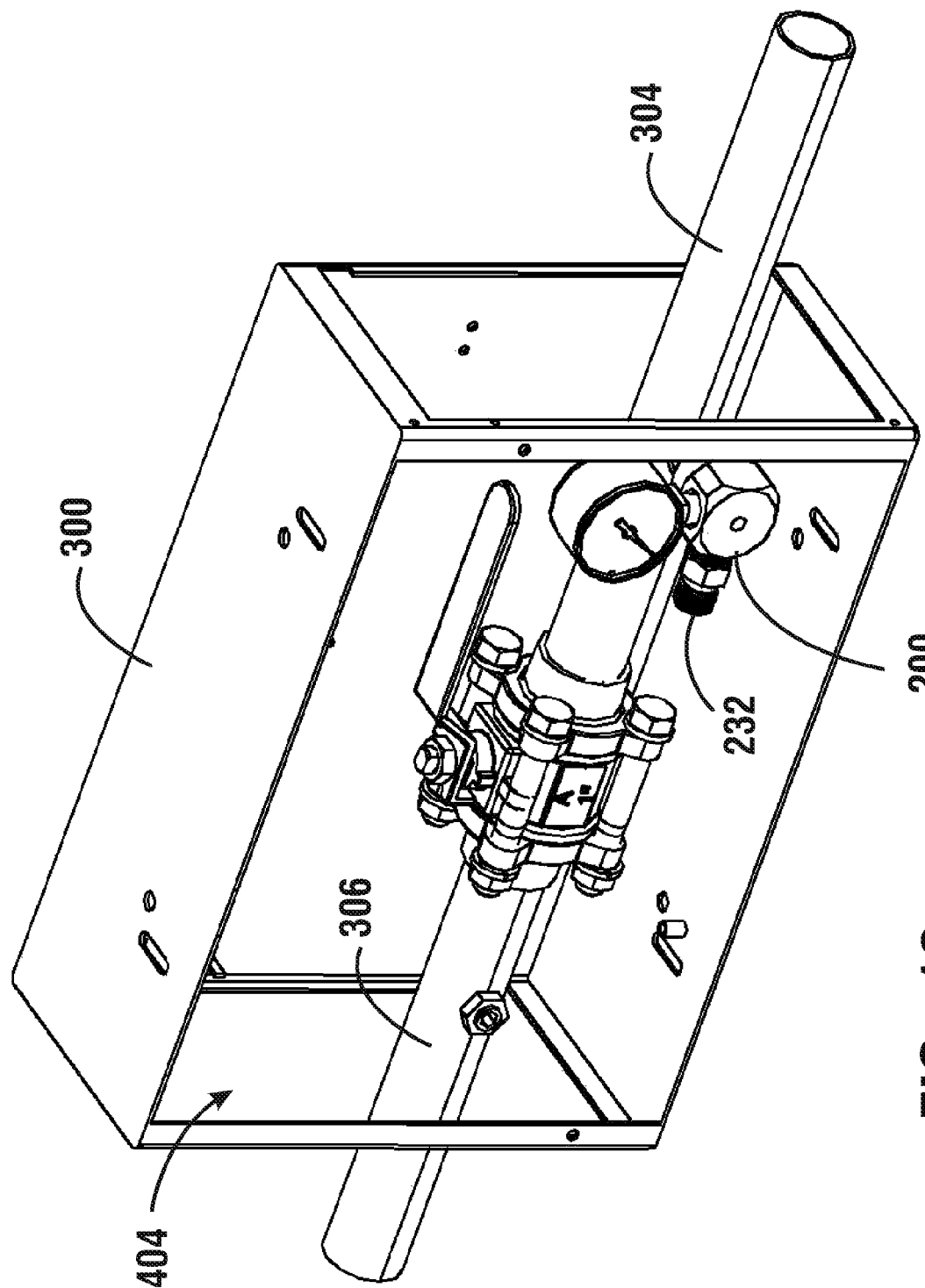
FIG. 13 shows a perspective view of the fitting mounted in the control panel.
Figure 14:
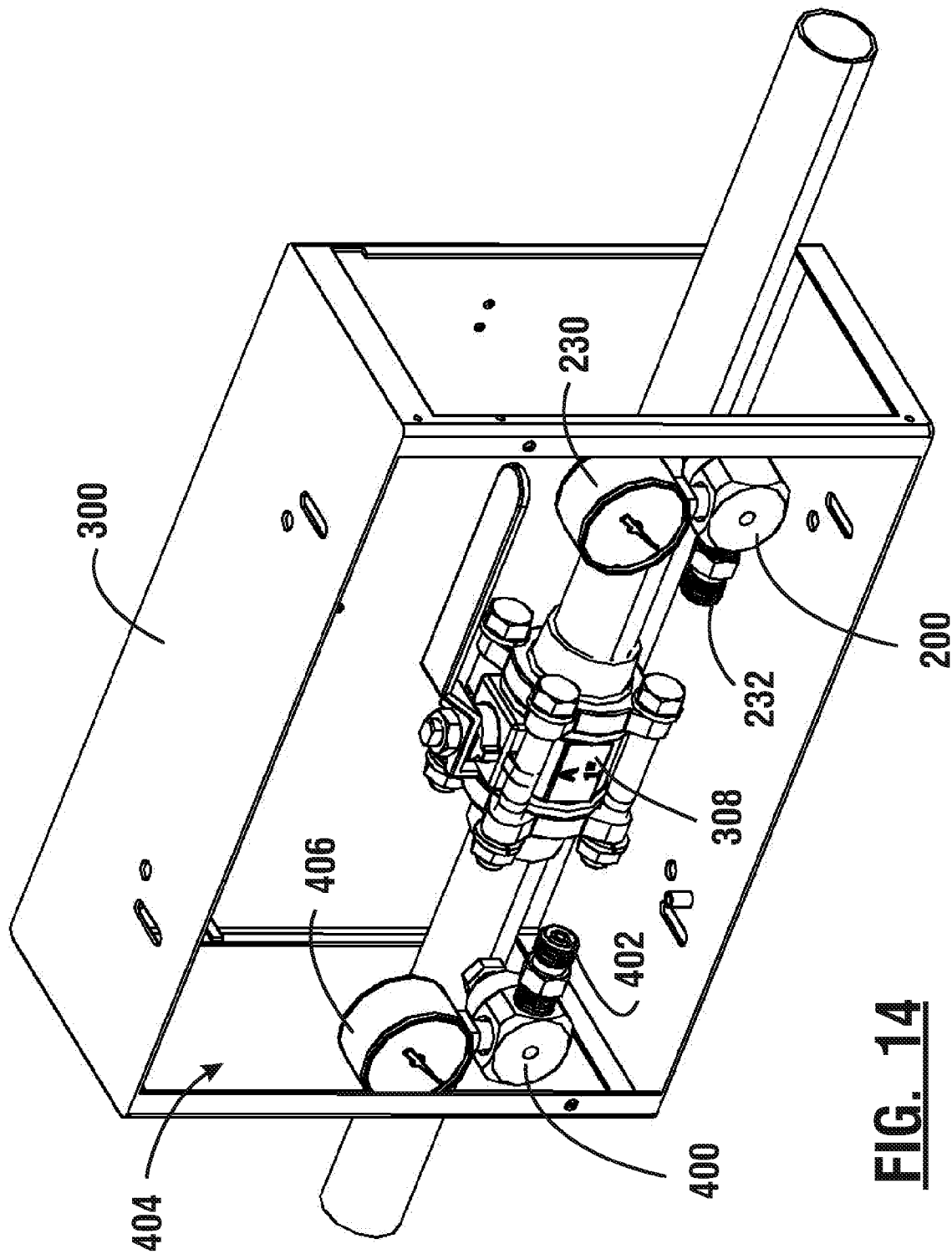
FIG. 14 shows a perspective view of two fittings mounted in the control panel on either side of a valve.

FIG. 13 shows a perspective view of the fitting 200 mounted in the control panel 300. FIG. 14 shows a perspective view of the control panel in which fittings 200, 400 have been mounted to both sides of the valve 308. As shown in FIGS. 13 and 14 the fitting(s) enable gas specific DISS threaded couplers 232 and 402, pressure gauges 230, 406, and other components to be mounted to an existing control panel without interfering with the operation of the valve 308 or without interfering with closing the cover mounted to close the opening 404 to the control panel.

As discussed previously the gas specific DISS threaded couplers mounted to the described fitting may be used for backfeeding medical gases into the piping system. When back feeding is necessary, the medical gas piping system does not need to be taken to atmosphere. Also, providing a gas specific DISS threaded coupler on one or both sides of the valve can reduce costs for future tie ins or remodeling work involving the medical gas piping system. For example, providing a gas specific DISS threaded coupler on one or both sides of the valve allows areas of the medical gas piping system to remain in service (thru backfeeding) while area(s) on the upstream side of the valve are being demolished or renovated.

Figure 15:
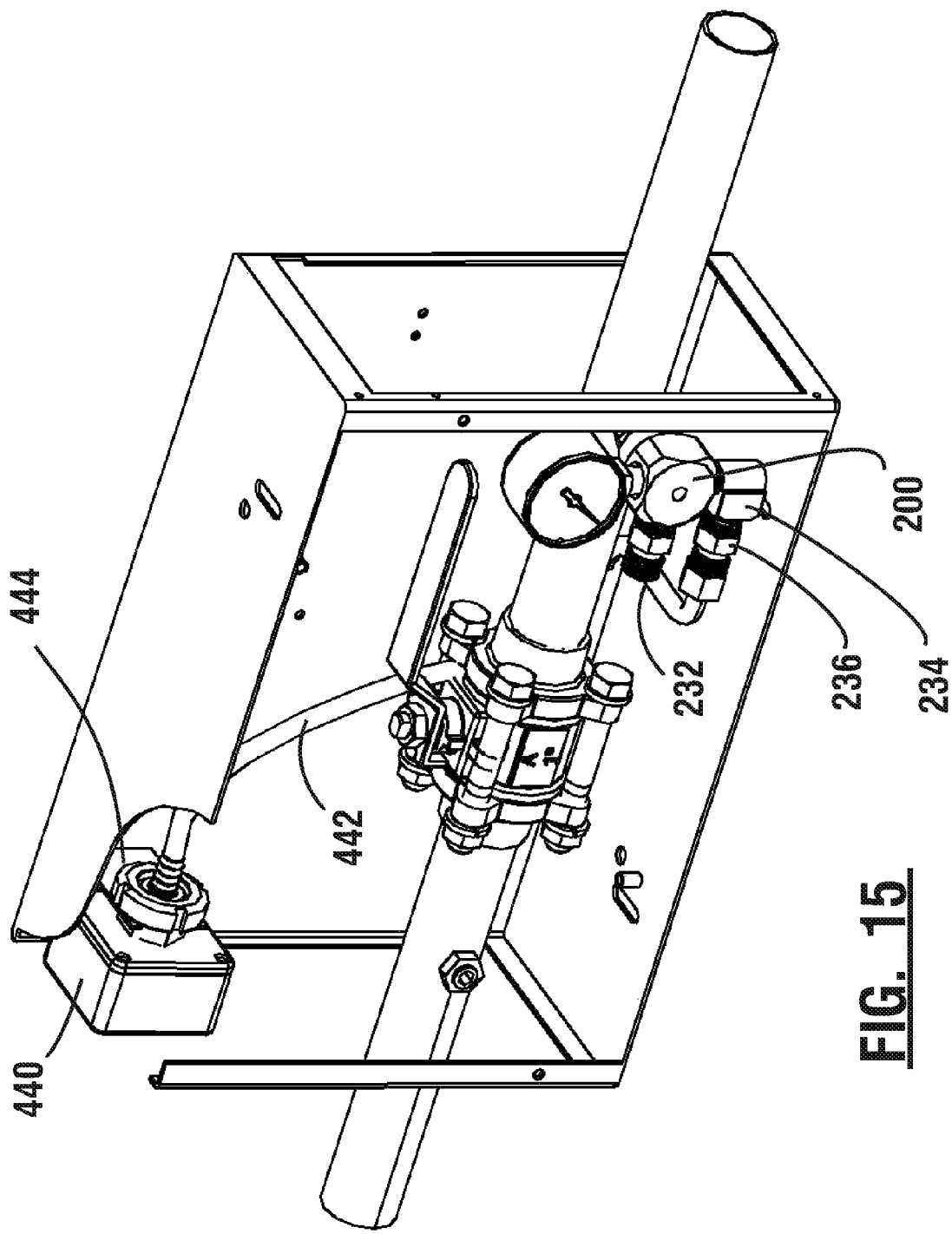
FIG. 15 shows a perspective view of a control panel that includes a transducer mounted via a hose to the fitting.

As shown in FIG. 15, in an exemplary embodiment, one or more transducers 440 may be mounted via a bracket 444 to an inside wall of the control panel or other location. A hose 442 or any other industry approved conduit may be placed in operative connection between the transducer 440 and a second DISS threaded coupler 236 connected to the fitting using the previously described elbow coupler 234. Such a transducer may be capable of monitoring characteristics of the medical gas such as pressure. Transducers connected to the medical gas system via the described fittings may be used in conjunction with a medical gas alarm to monitor and trigger an appropriate alarm when the pressure conditions of the medical gas pipeline are outside normal parameters. Mounting transducers in the control panel enables locating, required annual testing and servicing of the transducers to be performed faster and easier than traditional installation of transducers above a ceiling for example.

Although FIGS. 13 and 14 show only one gas specific DISS coupler attached to each fitting, it is to be understood that in these described embodiments, two gas specific DISS couplers may be mounted to each fitting such as shown in FIG. 15. In such embodiments, one of the gas or vacuum specific DISS couplers may be used to connect to a secondary gas or vacuum source while a second one of the gas specific DISS couplers may be mounted to a transducer in the control panel or a second source of the same gas. Also, although FIGS. 13 and 14 only show one valve in a control panel, the described fitting may be used in control panels with multiple valves such as that shown in FIG. 4.

In addition, the described fitting may be used to provide an existing control panel with gas specific immediate access to withdraw medical gas from the pipeline. For example, existing control panels are typically located in hallway areas or at nursing stations rather than in patient rooms or procedure areas. Installing the described fitting with a gas specific DISS threaded coupler to an existing control panel enables a temporary outlet or manifolded group of outlets such as a medical gas rail to be quickly connected to the control panel in order to provide medical gases to additional patients in hallways, waiting rooms and other areas near a control panel.

Figure 16:
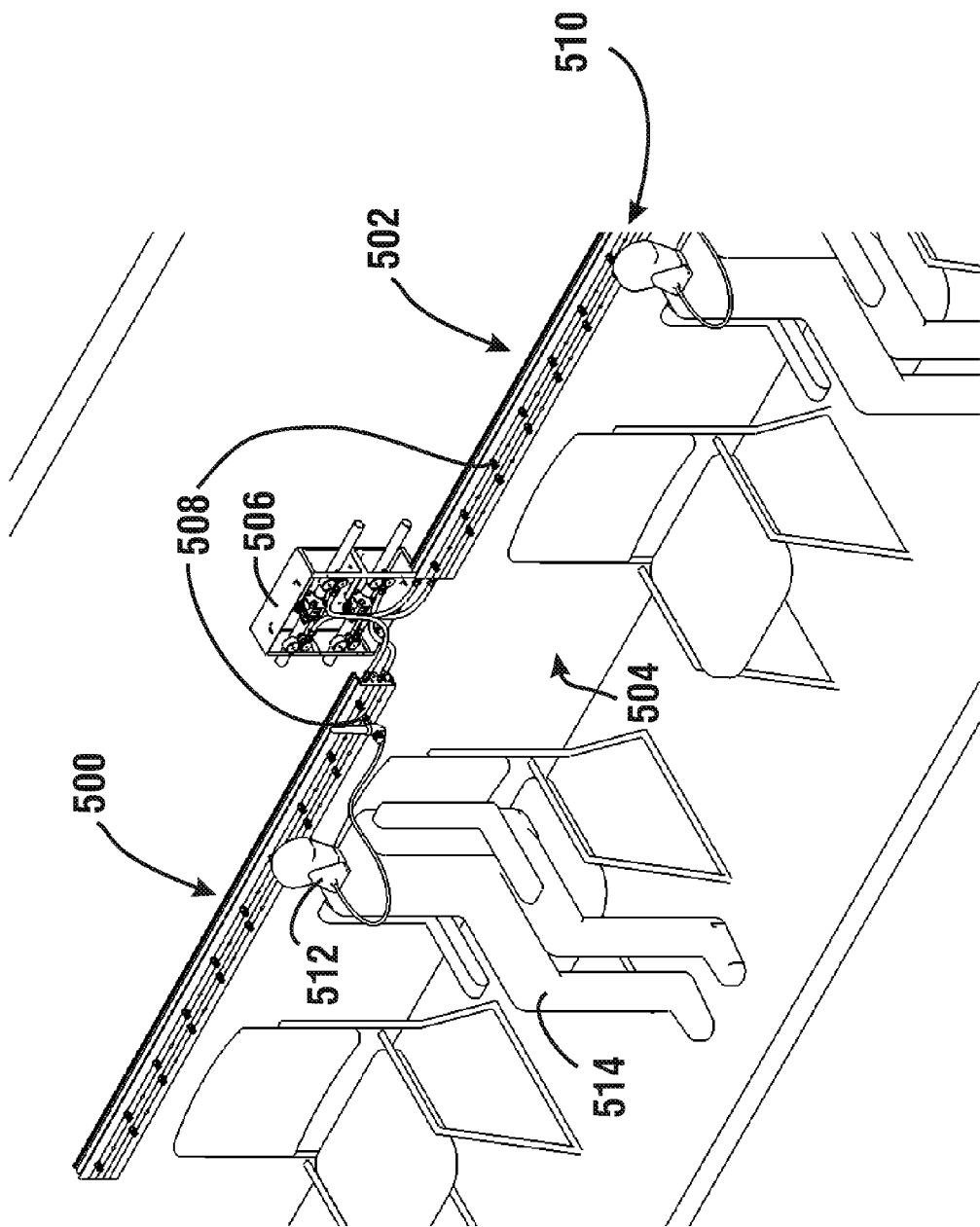
FIG. 16 shows an example of medical gas rails mounted to a hallway wall, which rails are in operative connection with the described fittings mounted in the control panel.

FIG. 16 shows an example of medical gas rails 500, 502 mounted to a hallway wall 504 and adjacent a control panel 506 which includes the described fittings with gas specific DISS threaded couplers. These rails may include a plurality of spaced apart outlet ports 508. In an emergency that produces a large influx of patients, the described medical gas rails may be connected to the DISS threaded couplers of the control panel to provide a supply of medical gas to the outlet ports 508 along the medical gas rails 500, 502. Patients 514 in a hallway or waiting room may then be positioned adjacent the rail(s) so as to quickly provide such patients with access to medical gases. In an exemplary embodiment, each rail is comprised of a plurality of parallel pipelines 510 each of which may be selectively coupled to a respective specific gas supply pipeline in the control panel 506. Each of the parallel pipelines of the rail may include a plurality of spaced apart outlet ports 508. In an emergency, gas delivery masks 512 may be placed in operative connection with the outlet ports to provide patients 514 with a supply of the medical gases from the outlet ports.

The exemplary embodiment described herein include particular structures to achieve the desirable results. Those having skill in the art may devise other embodiments with other structures which employ the same inventive principles encompassed by the subject matter as claimed.

Thus the exemplary embodiments achieves the above stated objectives, eliminates difficulties encountered in the prior methods, solves problems and attains the desirable results described herein.

In the foregoing description certain terms have been used for brevity, clarity and understanding. However, no unnecessary limitations are to be implied therefrom. Such terms are for descriptive purposes and are intended to be broadly construed. The descriptions and illustrations herein are by way of examples and the invention is not limited to the exact details shown and described.

In the following claims any feature described as a means for performing a function shall be construed as encompassing any means capable of performing the recited function. The means shall not be limited to the particular means shown as performing that function in the foregoing description or mere equivalents thereof.

Having described the features, discoveries and principles of embodiments, the manner in which it is constructed and operated, and the advantages and useful results attained; the new and useful structures, devices, elements, arrangements, parts, combinations, systems, operations, methods and relationships are set forth in the appended claims.

We claim:

1. A method of upgrading a control panel of a medical gas delivery system comprising an enclosure and a cover operative to close an opening to the enclosure, wherein the enclosure includes therein at least one valve and first and second pipelines in operative connection with each respective end of the at least one valve, wherein the first and second pipelines each include a front facing side which faces the opening to the enclosure, wherein the front facing side of the first pipeline includes a threaded opening therein, wherein a pressure gauge is mounted in the threaded opening:

a) removing the pressure gauge from the threaded opening of the first pipeline;

b) mounting a fitting to the threaded opening of the first pipeline, wherein the fitting includes a body and a threaded projection extending from the body, wherein the threaded projection is threaded into the threaded opening of the first pipeline, wherein the body includes at least two ports, wherein a first one of the ports includes a gas specific DISS threaded coupler mounted thereto, which extends from the fitting in a direction that is perpendicular to a longitudinal axis of the projection of the fitting, wherein a second one of the ports includes a second pressure gauge which extends from the fitting in a direction that is perpendicular to the longitudinal axis of the projection of the fitting, wherein when mounted to the threaded opening of the first pipeline, the fitting, the gas specific DISS threaded coupler, and the second pressure gauge do not extend through the opening of the enclosure.

2. The method according to claim 1, further comprising:

c) connecting a secondary gas source to the gas specific DISS threaded coupler, wherein the secondary gas source includes a pressure vessel with a valve, a regulator, and a mating specific threaded coupler adapted to mount to the gas specific DISS threaded coupler and place the secondary gas source in fluid communication with the first pipeline;

d) opening the valve on the pressure vessel;

e) delivering gas from the pressure vessel into the first pipeline;

f) closing the valve of the medical gas delivery system; and g) controlling the pressure of gas applied from the pressure vessel into the medical gas system through use of the regulator associated with the pressure vessel.

3. The method according to claim 1, wherein the fitting includes a third port in the body, wherein the third port is in operative connection with a second gas specific DISS threaded coupler which extends from the fitting in a direction that is perpendicular to a longitudinal axis of the projection of the fitting, and further comprising:

c) mounting a transducer inside the control panel;

d) placing the transducer in fluid communication with the second gas specific DISS threaded coupler;

e) monitoring at least one characteristic of the gas in the first pipeline through operation of the transducer.

4. The method according to claim 1, further comprising:

c) connecting a secondary gas outlet to the gas specific DISS threaded coupler, wherein the secondary gas outlet includes at least one outlet port and a mating specific threaded coupler adapted to mount to the gas specific DISS threaded coupler and place the secondary gas outlet in fluid communication with the first pipeline;

d) connecting a gas delivery mask to the at least one outlet port;

e) providing a medical gas to a patient through the gas delivery mask.

5. The method according to claim 4, wherein the secondary gas outlet includes a plurality of outlet ports, wherein each outlet port is mounted to a wall of a hallway, wherein further comprising:

f) connecting a plurality of a gas delivery masks to the plurality of outlet ports;

g) providing the medical gas to a plurality of patients through the gas delivery masks.

6. An apparatus comprising:

at least one fitting for use in a control panel of a medical gas delivery system, the at least one fitting comprising:

a body, including an internal cavity through which medical gases are capable of flowing;

a threaded projection extending from the body, wherein the threaded projection is adapted to connect to a threaded opening of a medical gas pipeline in the control panel, wherein the threaded projection includes an opening therein to the cavity in the body;

at least two ports in the body, wherein each of the ports includes an opening therein to the cavity in the body, wherein a first one of the ports is adapted to receive a gas specific DISS threaded coupler mounted thereto, which extends from the at least one fitting in a direction that is perpendicular to a longitudinal axis of the projection of the at least one fitting;

wherein a second one of the ports is adapted to receive a pressure gauge which extends from the at least one fitting in a direction that is perpendicular to the longitudinal axis of the projection of the at least one fitting, wherein the at least one fitting has a size, such that when the at least one fitting is mounted to the threaded opening of the medical gas pipeline, the at least one fitting places the gas specific DISS threaded coupler and the pressure gauge in positions which do not extend the DISS threaded coupler and the pressure gauge through an opening of an enclosure of the control panel.

7. The apparatus according to claim 6, further comprising:

the gas specific DISS threaded coupler in operative connection with the first one of the ports of the at least one fitting;

the pressure gauge in operative connection with the second one of the ports of the at least one fitting; and the control panel comprising the enclosure and the cover operative to close the opening to the enclosure, wherein the enclosure includes therein at least one valve and first and second pipelines in operative connection with each respective end of the at least one valve, wherein the first and second pipelines each include a front facing side which faces the opening to the enclosure, wherein the front facing side of the first pipeline includes the threaded opening therein, wherein the threaded projection of the at least one fitting is in operative connection with the threaded opening of the first pipeline, wherein the gas specific DISS threaded coupler and the pressure gauge do not extend through the opening of the enclosure of the control panel.

8. The apparatus according to claim 7, wherein the at least one fitting includes a third port in the body, wherein the third port includes an opening therein to the cavity in the body, wherein the third port is in operative connection with a second gas specific DISS threaded coupler which extends from the at least one fitting in a direction that is perpendicular to a longitudinal axis of the projection of the at least one fitting.

9. The apparatus according to claim 8, further comprising at least one transducer mounted inside the control panel, wherein the transducer is in fluid communication with at least one of the gas specific DISS threaded couplers.

10. The apparatus according to claim 7, further comprising at least one secondary gas outlet, wherein the secondary gas outlet includes at least one outlet port and a mating specific threaded coupler, wherein the mating specific threaded coupler is adapted to mount to the gas specific DISS threaded coupler and place the secondary gas outlet in fluid communication with the first pipeline.

11. The apparatus according to claim 10, wherein the secondary gas outlet includes a plurality of outlet ports, wherein at least one of the outlet ports is adapted to connect with a gas delivery mask and provide a medical gas to the gas delivery mask.

* * * * *